(12) United States Patent
Davidson

(10) Patent No.: US 6,235,251 B1
(45) Date of Patent: May 22, 2001

(54) SYSTEM AND METHOD FOR TREATING CELLS USING ELECTROMAGNETIC-BASED RADIATION

(76) Inventor: James G. Davidson, 280 Paul Dr., Paris, TN (US) 38242

(*) Notice: Subject to any disclaimer, the term of this patent is extended or adjusted under 35 U.S.C. 154(b) by 0 days.

(21) Appl. No.: 09/361,345

(22) Filed: Jul. 26, 1999

(51) Int. Cl.⁷ .............................. B01J 19/12; C12M 1/00; A61N 1/00
(52) U.S. Cl. ...................... 422/186.01; 600/9; 435/283.1
(58) Field of Search ................... 422/186.04; 435/283.1; 600/9, 13–15

(56) References Cited

U.S. PATENT DOCUMENTS 5,880,661 * 3/1999 Davidson et al. .................... 335/306
6,083,149 * 7/2000 Wascher et al. .......................... 600/9

OTHER PUBLICATIONS

Hulda Regehr Clark, "The Cure for All Diseases", New Century Press, pp. 5–30, 331–348, 457–512, 561–576, p (1995), No Month Available.
Richard E. Loyd, "Zappers and Other Gizmos", Turf's Electroherbalism Homepage, Internet location www.mindspring.com/~turf/alt/elec/gizmos.txt., pp. 1–4, Jan., 1998.
Turf, "Electrical and Frequency Effects on Pathogens", Turf's Electroherbalism Homepage, Internet location www-.mindspring.com/~turf/alt/elec/elecpath.txt., pp. 1–6.
David Doody, et al., "Basics of Space Flight Learner's Workbook", Jet Propulsion Laboratory–NASA, California Institute of Technology web site, Internet address www.jpl-.nasa.gov/basics, Chapter 6, Section 1, document JPL–D–9774, Rev. A, Dec. 1995.
Richard Leviton, "Killing Cancer Cells with Magnetic Energy"Alternative Medicine Homepage, Internet address www.alternativemedicine.com/digest/issue20/i20–a78.shtml, issue 20, pp. 1–10.
Turf, "Who is Hulda Clark?", Truf's Electroherbalism Homepage, Internet address www.mindspring.com/~turf/alt/gen/huldawho.txt, pp. 1–4.

* cited by examiner

Primary Examiner—Kathryn Gorgos
Assistant Examiner—Thao Tran
(74) Attorney, Agent, or Firm—Jenkens & Gilchrist, P.C.

(57) ABSTRACT

A device for treating cells is disclosed. The device includes a plurality of permanent magnets arranged in a side-by-side relationship with the magnetic north pole and the magnetic south pole of each permanent magnet being adjacent the magnetic north pole and magnetic south pole of an adjacent permanent magnet, respectively, the plurality of permanent magnets forming a ring of permanent magnets. The device further includes an electrically conductive wire wound substantially around the ring of permanent magnets, and tubing wrapped around the ring of permanent magnets between windings of the wire. A cooling device introduces a flow of coolant through the tubing so as to substantially cool the device. The device further includes a control circuit, connected to the wire, for selectively generating a coil current for passing through the wire. The current has an AC component and a DC component. The frequency of the AC component is programmable and is set to substantially match a resonant frequency associated with the cells to be treated. The coil current creates an electromagnetic field that interacts with a magnetic field generated by the ring of permanent magnets to generate a complex field that causes ionic collisions within the cells to be treated.

25 Claims, 8 Drawing Sheets

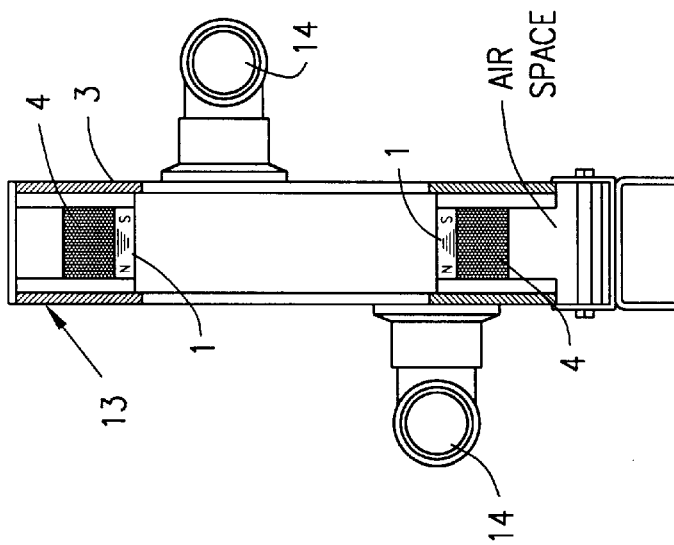
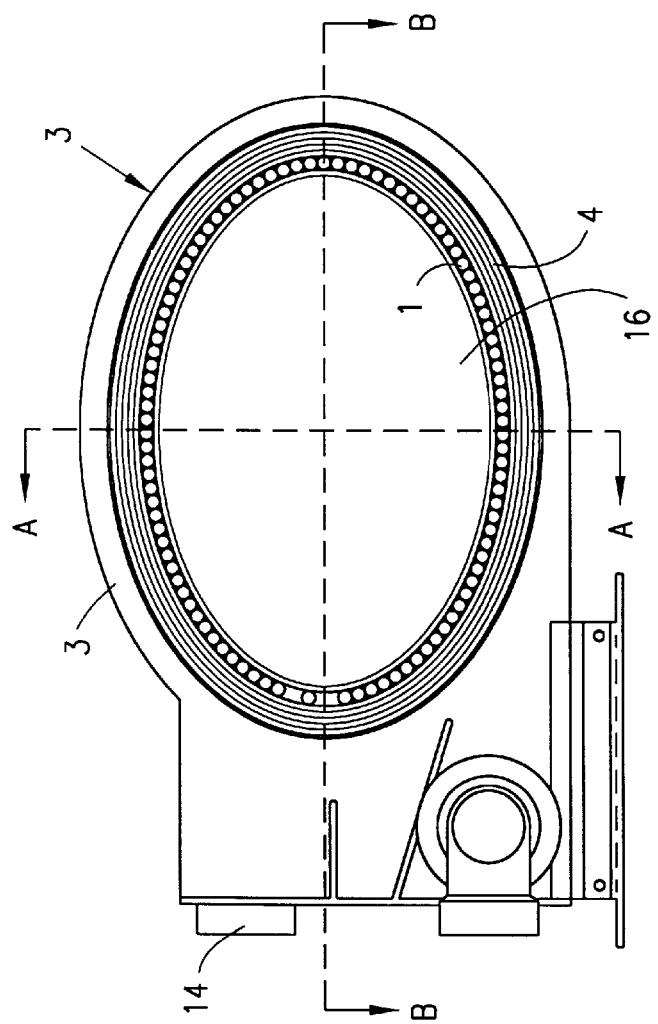
FIG. 8
FIG. 7

SYSTEM AND METHOD FOR TREATING CELLS USING ELECTROMAGNETIC-BASED RADIATION

BACKGROUND OF THE INVENTION

1. Technical Field of the Invention

The present invention relates to a device for treating cells, and particularly to a device which generates a complex electromagnetic-based field that substantially destroys the cells when applied thereto.

2. Background of the Invention

Since the early part of the twentieth century, attempts have been undertaken to treat or otherwise cure human ailments using electricity. One of the first researchers in this field of treatment, Royal Rife, discovered that certain lower life forms could be adversely affected upon exposure to electromagnetic radiation having certain frequencies. Using a frequency generator, Rife claimed to have treated and otherwise destroyed a number of live viruses, bacteria and other potential pathogens. Cells exposed to Rife's frequency generator were said to lose their mobility, pleomorph into different forms or actually burst. It has been claimed that each type of cell, including the many viral and cancer cells, has a unique resonant frequency such that a cell is substantially destroyed when radiated with a field, such as an electromagnetic field, having a frequency which substantially matches the cell's resonant frequency.

Following Rife's work, numerous devices have been created which generate signals or fields at a desired frequency for treating cells or other organisms. Some devices create signals and/or fields having DC and AC components, create signals and/or fields having varying frequencies, or utilize coils of wire for creating an electromagnetic field in which the cells to be treated are placed.

Prior devices, however, are not without their shortcomings. Many prior devices are based upon crude designs, which sometimes led to imprecise signal and field generation and even harmful treatments. In part due to the imprecise operation of the prior devices, the successful treatment of a wide variety of cells and other organisms was relatively infrequent and required prolonged use of the prior devices. As a result, there is a need for a device for successfully treating cells, organisms, and various human conditions in an efficient, precise and timely manner.

SUMMARY OF THE INVENTION

The present invention overcomes the shortcomings in prior systems for generating electromagnetic radiation and satisfies a significant need for a system which generates electromagnetic radiation at frequencies for treating a number of different types of cells and other organisms.

According to a preferred embodiment of the present invention, there is provided a device for generating electromagnetic-based radiation, including a plurality of cylindrical permanent magnets arranged in a side-by-side relationship. The longitudinal axes of the permanent magnets are parallel to each other. The magnetic north pole of a permanent magnet is situated adjacent the magnetic north poles of the permanent magnets adjacent thereto. Likewise, the magnetic south pole of a permanent magnet is situated adjacent the magnetic south poles of the permanent magnets adjacent thereto. With the magnetic north pole and magnetic south pole of each permanent magnet being situated adjacent the magnetic north pole and magnetic south pole of adjacent permanent magnets, respectively, the normally elliptical magnetic field of each permanent magnet is elongated or otherwise distorted along the longitudinal axis thereof. The aligned permanent magnets form a substantially elliptically shaped ring of permanent magnets.

The elliptically shaped ring of permanent magnets includes two or more gaps between adjacent permanent magnets. The gaps in the ring of permanent magnets establish a pulsating magnetic field and thereby promote effective control thereover.

At least one wire of electrically conductive material is wrapped around the elliptically shaped ring of permanent magnets to form a coil. The number of turns or windings may vary depending in part upon the desired application of the present system. For instance, the number of turns may be 100, 200, 300 or 400. The wire is adapted to carry an electric current therethrough so as to establish an electromagnetic field relative to the permanent magnet ring and interact with the magnetic field generated thereby.

In addition, tubing capable of carrying a flowable coolant is wrapped around the ring of permanent magnets within the coil of wire. By introducing a flow of a water-based fluid through the tubing, heat generated from the flow of current through the wire is controlled and the flux of the magnetic field through the center portion of the magnet ring is promoted. The preferred embodiment of the present invention further includes a pump device and condenser unit in fluid communication with the tubing so as to introduce a flow of cooled fluid therethrough.

The preferred embodiment of the present invention further includes a control circuit for generating a current for passing through the wire. The control circuit includes a rectifier circuit for receiving a three phase AC input and generating a substantially DC output voltage. The control circuit further includes a frequency changer circuit which receives the three phase AC input and generates an AC output signal having a variably-controlled frequency. The cumulative current provided to the wire is the sum of the outputs of the rectifier circuit and the frequency changer circuit, including an AC component and a DC component. In an exemplary embodiment of the present invention, the DC component of the current applied to the wire is at a voltage level that exceeds the peak-to-peak voltage of the AC component of the current. The control circuit further includes a switching circuit for selectively switching the DC output of the rectifier circuit between positive and negative voltage levels, relative to a ground potential.

In use, the frequency changer circuit is initially set to generate an AC signal having a frequency which substantially matches the resonant frequency of the cell or other material which the preferred embodiment of the present invention is intended to treat. The pump device and the condenser unit are activated to pump a coolant, such as a water-based fluid, through the tubing. With the control circuit activated, the output current signal generated thereby is passed through the coil of wire in a first direction. Due to the inductive nature of the coil, an electromagnetic field is generated by the current which is either in the direction of the magnetic field generated by the permanent magnets or in an opposed direction thereto. In the event the electromagnetic field is in the same direction as the magnetic field, the resulting complex field may be seen as the sum of the electromagnetic field and the magnetic field. Alternatively, the complex field is seen as the difference between the electromagnetic field and the magnetic field.

The resulting cumulative complex field causes positive ions to be charged and to be located along the outer surface of its cell. After a sufficient amount of time has elapsed, the switching circuit of the control circuit is then toggled to a state so as to reverse the polarity of the DC component of the control circuit output relative to ground. The resulting output signal of the control circuit causes current in the wire to flow in the opposite direction as before, but at the same frequency. The electromagnetic field generated by the current in the coil reverses its direction. The resulting complex field is thereby caused to reverse its direction. Now subject to a complex field having a reversed direction, the charged positive ions collide with other ions in the cell or with other matter. The ionic collision has been seen to significantly adversely affect or otherwise destroy the cell or other material. Repetitive treatments have been observed to substantially destroy substantially all cells of the same type (having the same resonant frequency) in an individual's body.

BRIEF DESCRIPTION OF THE DRAWINGS

A more complete understanding of the system and method of the present invention may be obtained by reference to the following Detailed Description when taken in conjunction with the accompanying Drawings wherein:

FIG. 7 is a second side elevational view of a portion of the preferred embodiment of the present invention;

FIG. 8 is a cross-sectional view of the embodiment portion of FIG. 7 taken along the A—A line thereof;

DETAILED DESCRIPTION OF THE PREFERRED EXEMPLARY EMBODIMENTS

The present invention will now be described more fully hereinafter with reference to the accompanying drawings in which a preferred embodiment of the invention is shown. This invention may, however, be embodied in many different forms and should not be construed as being limited to the embodiment set forth herein. Rather, the embodiment is provided so that this disclosure will be thorough and complete, and will fully convey the scope of the invention to those skilled in the art.

Figure 1:
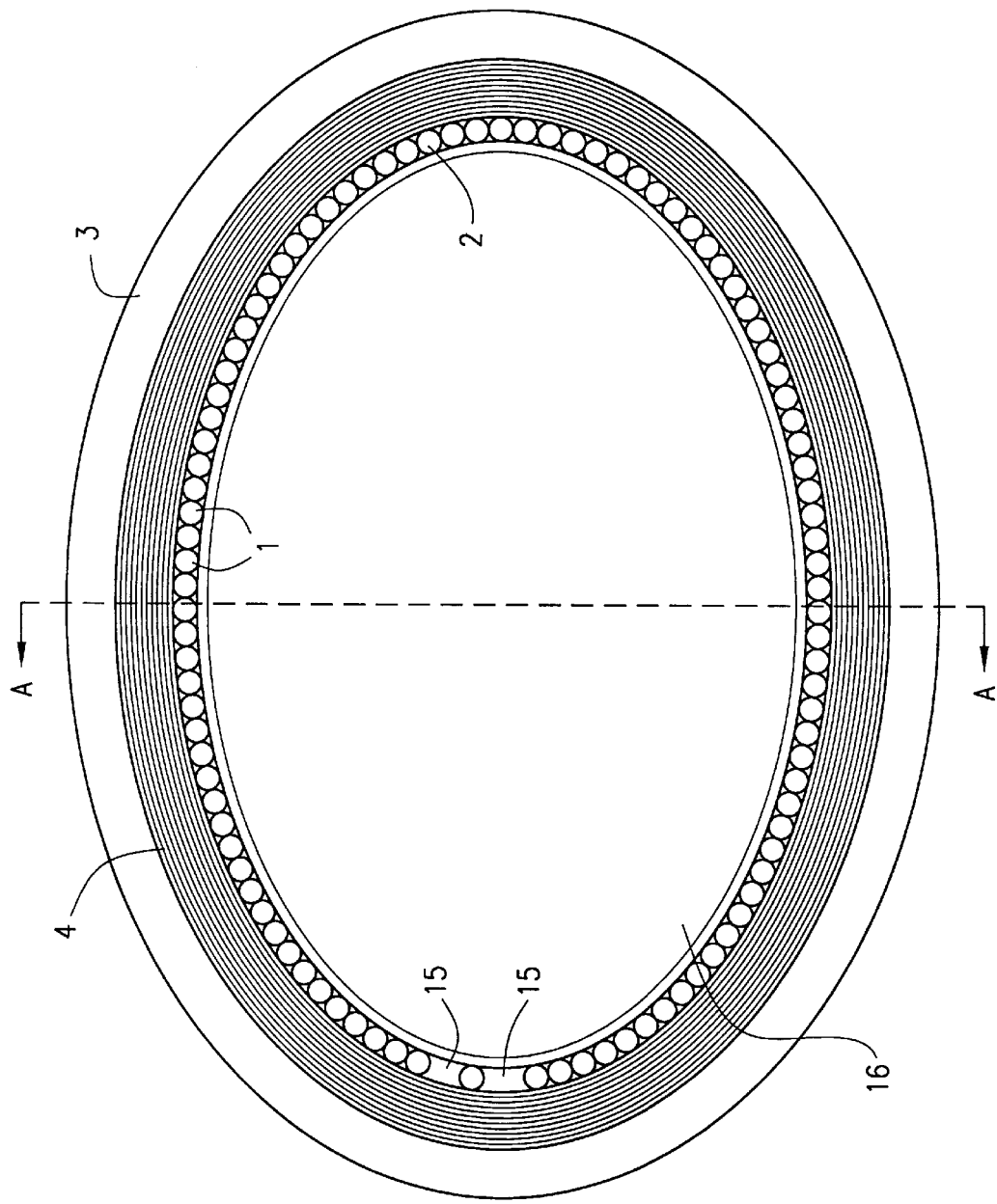
FIG. 1 is a side elevational view of a portion of the preferred embodiment of the present invention.
Figure 2:
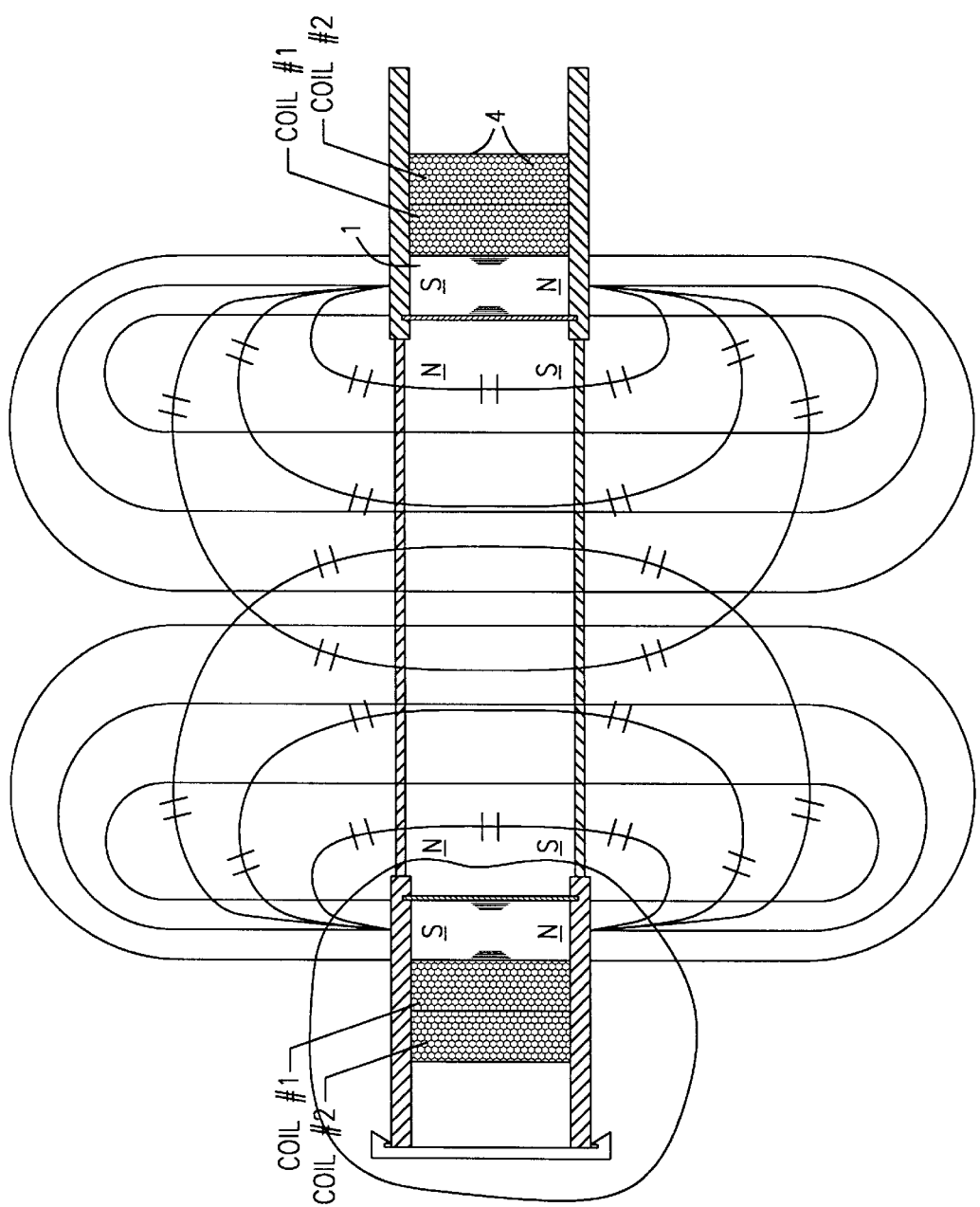
FIG. 2 is an elevational view of a portion of the preferred embodiment of the present invention generating various fields taken along the A—A line of FIG. 1.
Figure 3:
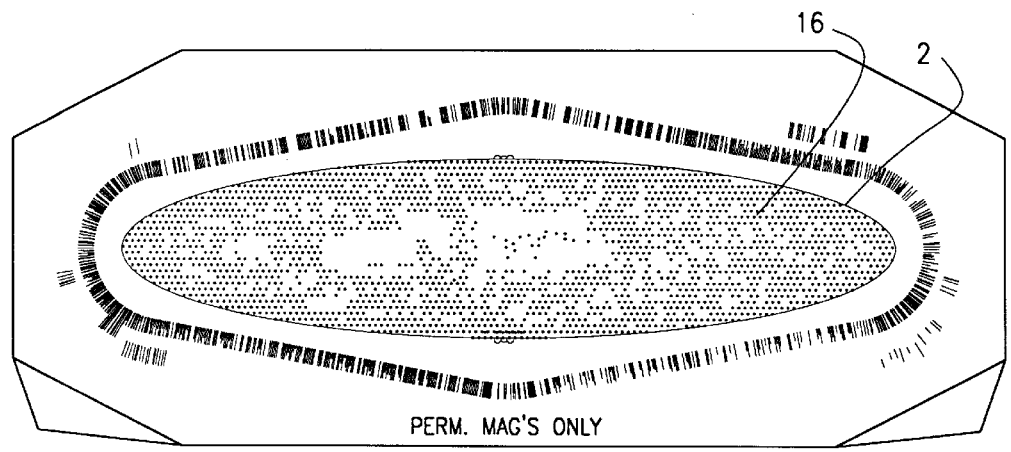
FIG. 3 is a graphic representation of an iron filing sculpture produced by a magnetic field that is generated by a preferred embodiment of the present invention.

Referring to FIGS. 1–12, there is shown an electromagnetic-based field generating device according to a preferred embodiment of the present invention. The electromagnetic-based field generating device includes a plurality of permanent magnets 1 arranged in a side-by-side relationship to each other so as to form an elliptical ring 2. Each permanent magnet 1 is preferably cylindrical or otherwise elongated, having a north pole at one end and a south pole at the opposite end. Permanent magnets 1 are aligned within the ring 2 such that the north pole and south pole of each permanent magnet 1 are adjacent to the north pole and south pole of an adjacent permanent magnet 1, respectively. The longitudinal axis of each permanent magnet 1 is parallel to the longitudinal axis of the other permanent magnets 1. This alignment of north poles and of south poles causes the magnetic field generated by each permanent magnet 1 to be altered from its normal substantially elliptical shape to be more elongated along the longitudinal axis of permanent magnet 1 as illustrated in FIG. 2. As can be seen in FIG. 3, which shows an iron filings sculpture responsive to the magnetic field generated by permanent magnets 1, the flux lines of the magnetic field generated by permanent magnets 1 is substantially uniformly distributed about the inner portion 16 of ring 2. Ring 2 of permanent magnets 1 is preferably held in a fixed placement within frame 3.

The preferred embodiment of the present invention further includes one or more wires 4 of electrically conductive material wrapped around ring 2 of permanent magnets 1 so as to form one or more coils. Wire 4 is adapted to carry a current to generate an electromagnetic field within the inner portion of ring 2. The number of windings or turns of coil 4 may vary depending in part upon the desired cumulative field generated by the present device.

An electromagnetic field generated by current flowing through wire 4 is a substantially circular electromagnetic field surrounding ring 2 and wire 4 that is truncated (FIG. 4) in part by the alignment of permanent magnets 1.

It is understood that a plurality of wires 4 may be wrapped around ring 2 and be capable for generating an electromagnetic field. FIG. 2 shows windings or coils of two separate wires 4 wound about ring 2.

Figure 5:
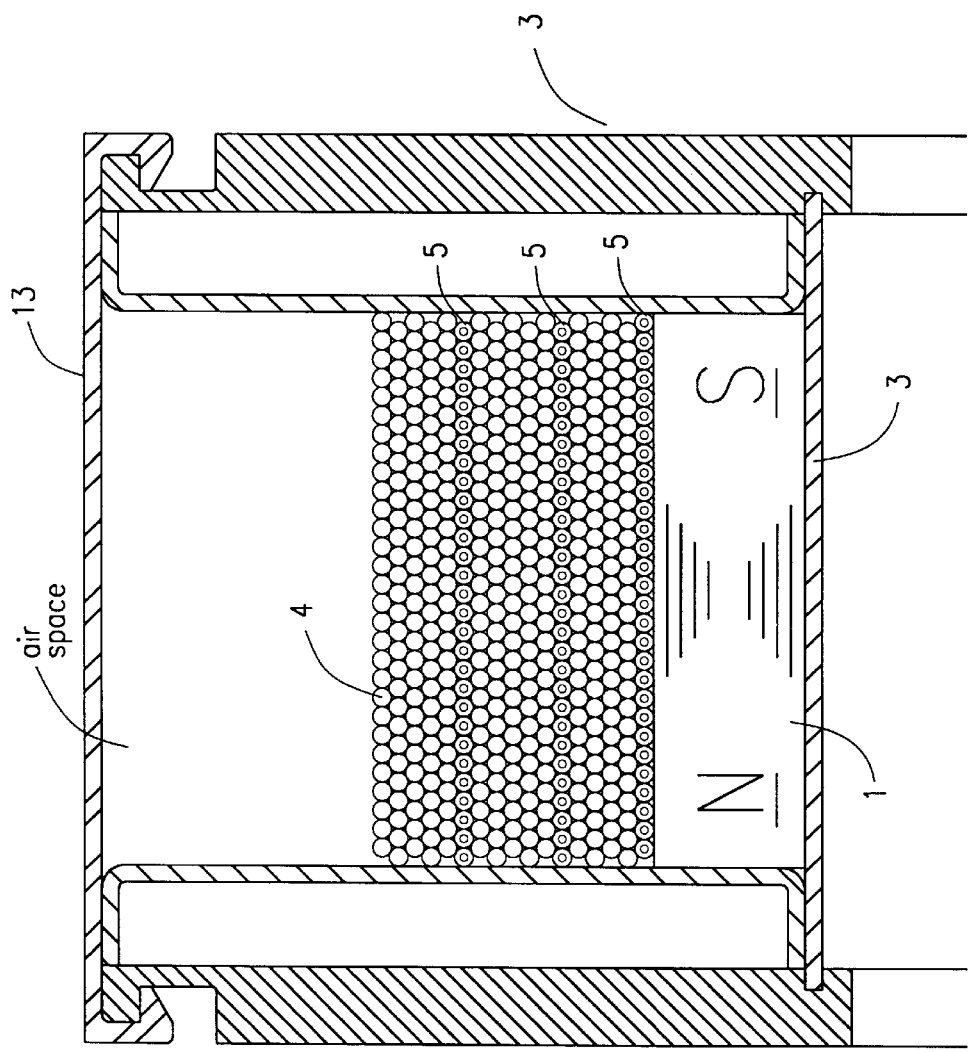
FIG. 5 is an enlarged elevational view of the circled portion of FIG. 2.

In order to reduce the build up of heat within the coil of wire 4 and ring 2, tubing 5 capable of carrying a flowable coolant therein is preferably wound around ring 2 much in the same way wire 4 is would around ring 2. Windings of tubing 5 are preferably spaced throughout the windings of wire 4, as shown in FIG. 5. A first winding or set of windings of tubing 5 is preferably disposed substantially against permanent magnets 1, with subsequent windings or sets of windings of tubing 5 being substantially evenly disposed at various positions within the windings of wire 4. Tubing 5 is preferably constructed from copper or other similar material.

The preferred embodiment of the present invention further includes a condenser 6 for cooling a fluid and pump 7 (FIG. 6) in fluid communication with tubing 5 and condenser 6 for imparting a flow of cooled fluid through tubing 5.

As stated above, by passing a cooled fluid through tubing 5, the temperature of the coil of wire 4 and permanent magnets 1 are reduced. Passing a water-based fluid through tubing 5 provides an additional benefit to the present invention. In particular, because tubing 5 is disposed within the windings of wire 4 and hence in the pathway of the electromagnetic field generated thereby, the presence of tubing 5 causes an excitation of the electromagnetic field which prevents the electromagnetic field from forming hysteresis.

Figure 6:
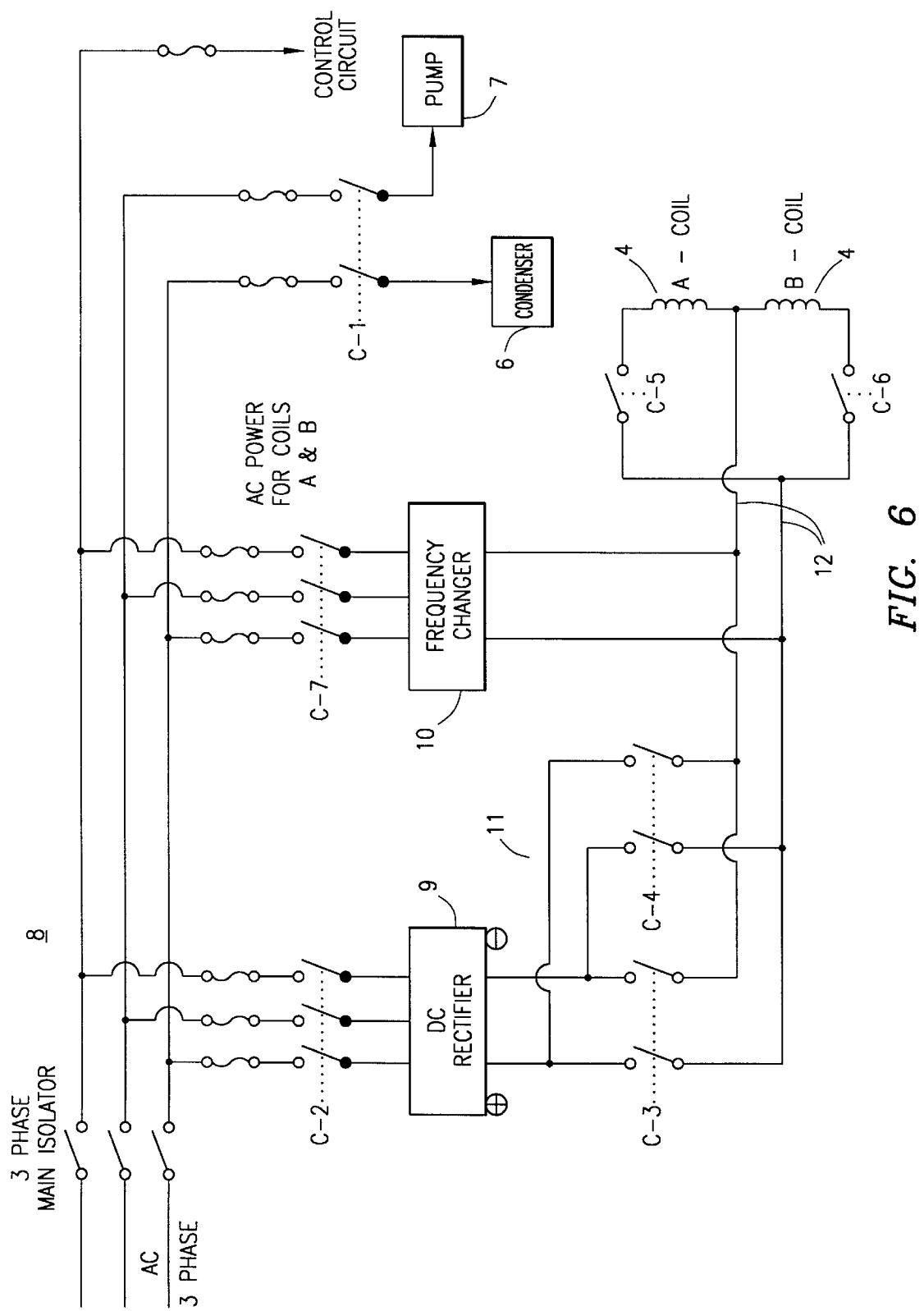
FIG. 6 is a schematic block diagram illustrating the control circuit according to a preferred embodiment of the present invention.

The preferred embodiment of the present invention further includes a control circuit 8 for controlling the operation of the present field generating device. Referring to FIG. 6, control circuit 8 includes a rectifier circuit 9 which receives three phase AC input lines and generates a DC current level. Control circuit 8 further includes a frequency changer circuit 10 which receives the three phase AC input lines and generates an AC signal having a variably-controlled and/or programmable frequency. The range of frequencies for the AC signal generated by frequency changer circuit 10 may be, for instance, between approximately 2 kHz and 9 kHz. It is understood, however, that frequency changer circuit 10 may allow the output thereof to be set to virtually any frequency. In a preferred embodiment of the present invention, the DC output level of rectifier circuit 9 and the AC peak-to-peak level of frequency changer 10 are programmable.

As shown in FIG. 6, the output signal 12 of control circuit 8 is the cumulative sum of signals from the output of rectifier circuit 9 and frequency changer circuit 10. Accordingly, control circuit output signal 12 is a signal having a DC component (generated by rectifier circuit 9) and an AC component (generated by frequency changer circuit 10).

Control circuit 8 further includes switching circuit 11 connected to rectifier circuit 9. Switching circuit 11 may be controlled to switch the output terminals of rectifier circuit 9 relative to the output of control circuit 8 so that the DC component of the output signal 12 is selectively reversible between a positive DC level and a negative DC level. In the event the peak-to-peak voltage difference of the AC signal generated by frequency changer circuit 10 is less than the DC output level generated by rectifier circuit 9, the output signal 12 of control circuit 8 is selectively switchable between a signal having a positive current and a signal having a negative current. As can be seen in FIG. 6, the output signal 12 of control circuit 8 is applied to wire 4.

Ring 2 of permanent magnets 1 preferably includes two or more gaps 15 or spaces 15 between adjacent permanent magnets 1, as shown in FIG. 1. Because in an inductive circuit the current has a tendency to be different based up on the degree of inductance of the environment in which the current travels, currents passing in proximity to gaps 15 are altered so as to cause excitations or energy bursts in the current and hence into the electromagnetic field generated thereby. these bursts in the electromagnetic field allow for the focusing of the electromagnetic field within a specific target area.

According to the preferred embodiment of the present invention, frame 3 provides a housing around magnetic ring 2, wire 4 and tubing 5. Frame 3 preferably covers the inner surface and side surfaces of ring 2, wire 4 and tubing 5. A lid 13 is preferably removably attached to frame 13 so as to cover an outer surface of wire 4 and tubing 5, as shown in FIG. 5. Lid 13 is preferably spaced from the outermost windings of wire 4. The air space between wire 4 and lid 13 allows for a flow of air within frame 3 for cooling wire 4. A plurality of air ducts 14 disposed substantially uniformly about frame 3 (FIGS. 7 and 8) provide fluid communication to the air space within frame 3.

Figure 10:
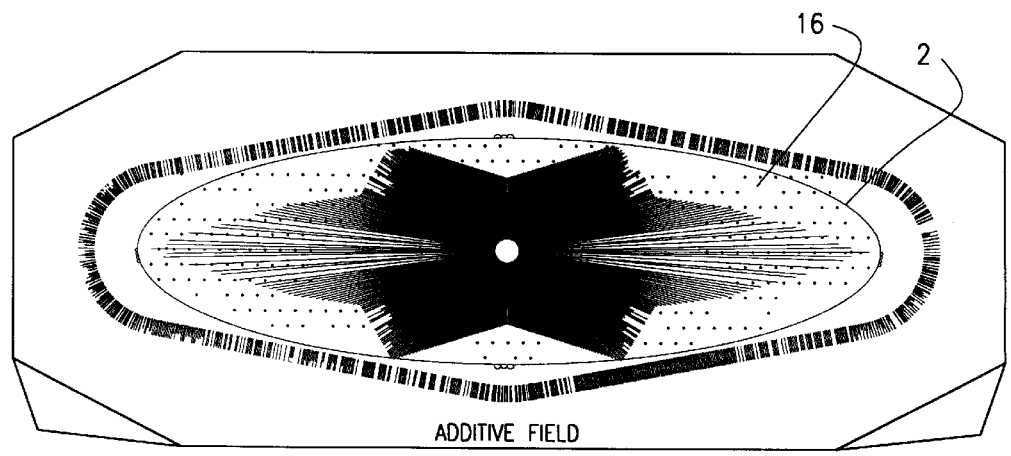
FIG. 10 is a graphic representation of an iron filing sculpture produced by a cumulative complex field generated by the preferred embodiment of the present invention.
Figure 4:
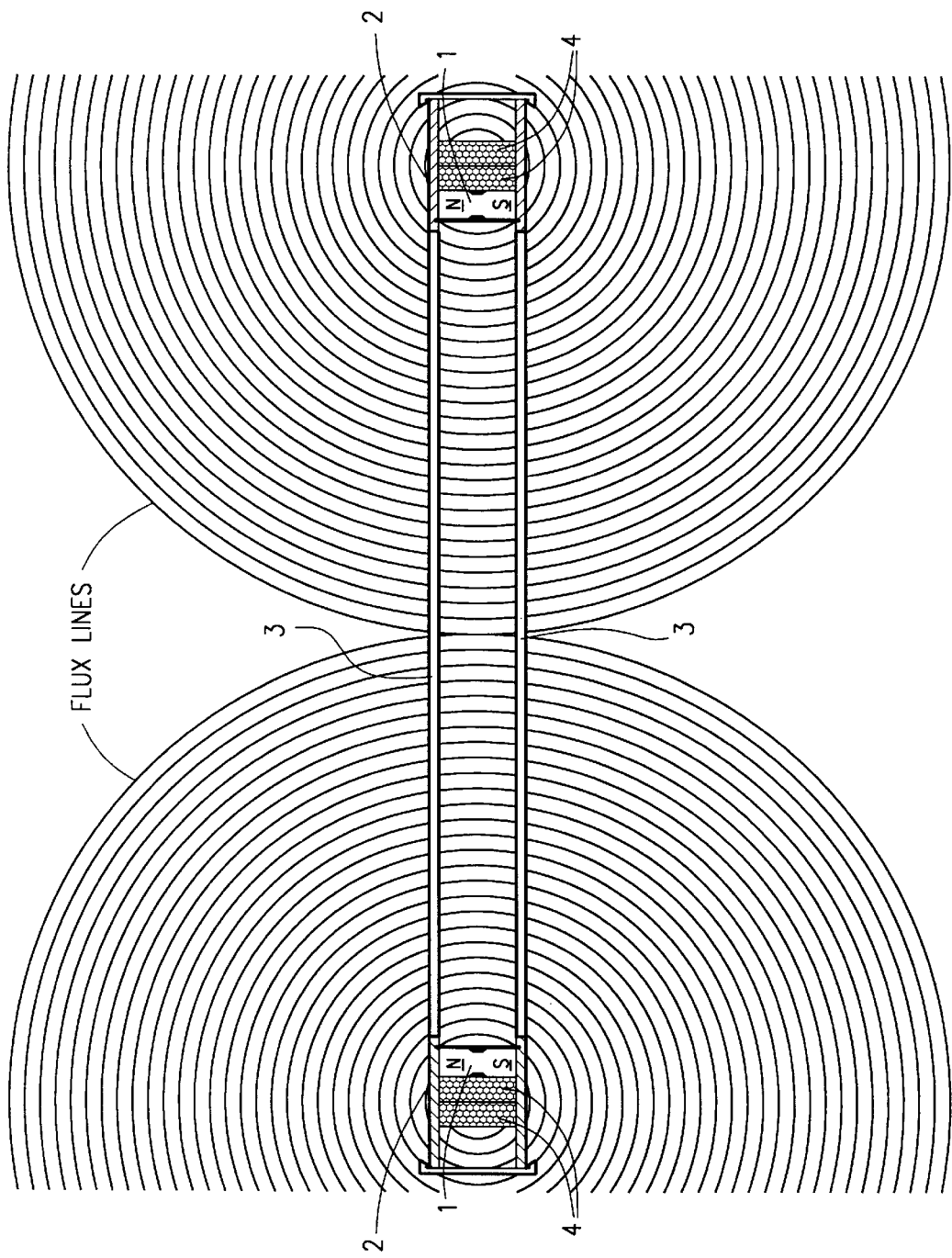
FIG. 4 is an elevational view of a portion of the preferred embodiment of the present invention taken along the A—A line of FIG. 1.
Figure 9:
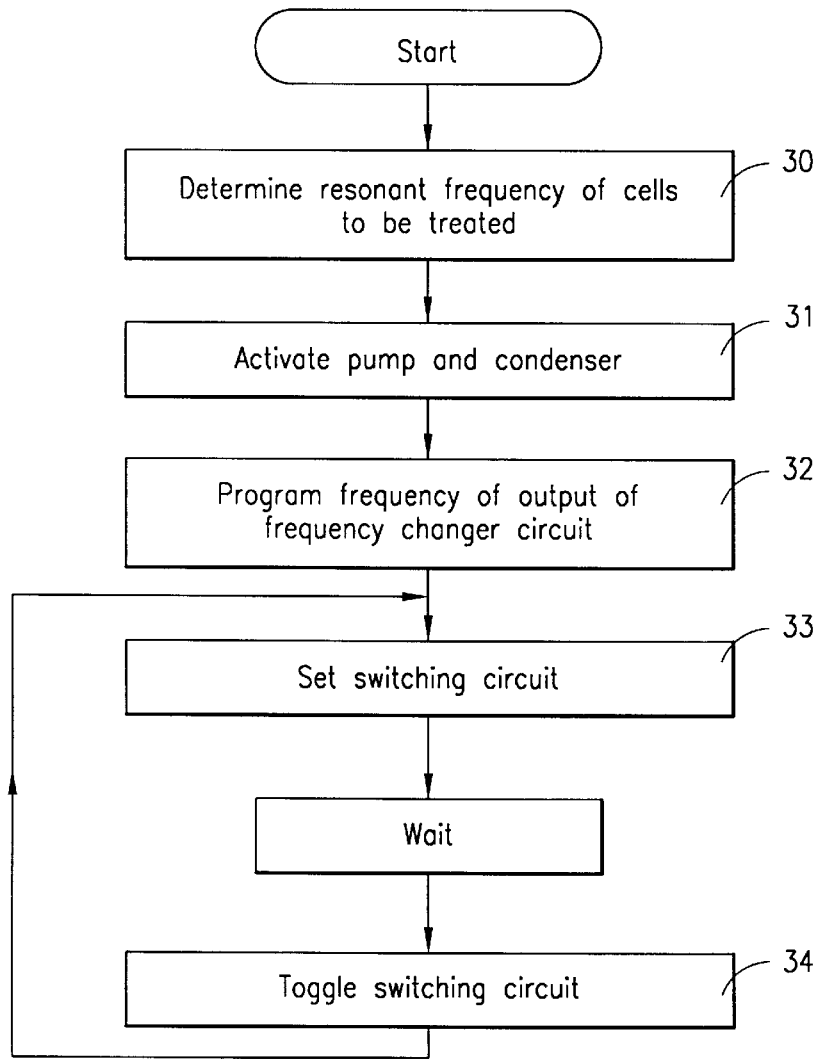
FIG. 9 is a flow chart illustrating an operation of the preferred embodiment of the present invention.

The operation of the electromagnetic-based field generating device according to the present invention will be described with reference to FIG. 9. Initially, the resonant frequency of the type of cell or other organism to be treated is determined at step 31. Next, condenser 6 and pump 7 are activated at step 31 to introduce a flow of a cooled, water-based fluid through tubing 5. Frequency changer circuit 10 is programmed at step 32 so that the AC component of the output signal 12 of control circuit 8 has a frequency which substantially matches the resonant frequency of the cell determined during step 30. Switching circuit 11 is controlled at step 33 so that the DC component of the output signal 12 of control circuit 8 has the desired polarity. In the present exemplary operation, switching circuit 11 is set so that the output signal 12 of control circuit 8 generates an electromagnetic field which is in the same direction as the magnetic field generated by the ring 2 of permanent magnets 1. Consequently, the electromagnetic field generated by control circuit 8 and the magnetic field generated by permanent magnets 1 are additive to form a complex field having an increased number of lines of flux passing through the inner portion of ring 2. FIG. 10 depicts this flux increase by illustrating an iron filing diagram when the electromagnetic field and the magnetic field are additive. With the cells to be treated being disposed within the inner portion of ring 2, the cells are subjected to this resulting cumulative complex field.

Figure 11:
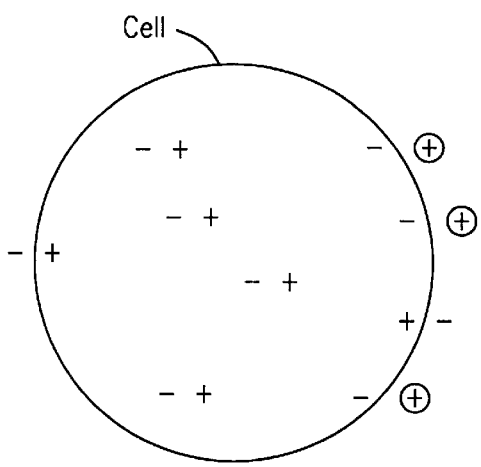
FIG. 11 illustrates the structure of a cell under treatment by the preferred embodiment of the present invention.

At this time, the cumulative complex field generated by control circuit 8 and permanent magnets 1 has an alternating portion having a frequency which substantially matches the resonant frequency of the cells to be treated. The cumulative complex field acts on the cells to charge the positive ions so that the positive ions appear at the outer portions of the cells along a first side thereof, as illustrated in FIG. 11.

After a period of time has elapsed so that the positive ions are suitably charged, switching circuit 11 is toggled at step 34 to reverse the polarity of the DC level of the output generated by rectifier circuit 9. This results in the DC component of the output signal 12 of control circuit 8 having a reversed polarity. Assuming that the absolute value of the DC component level of output signal 12 is greater than the peak-to-peak level difference of the AC component thereof, the output signal 12 and thus the current flowing through wire 4 have a reversed current level relative to the initial current level provided to wire 4.

Figure 12:
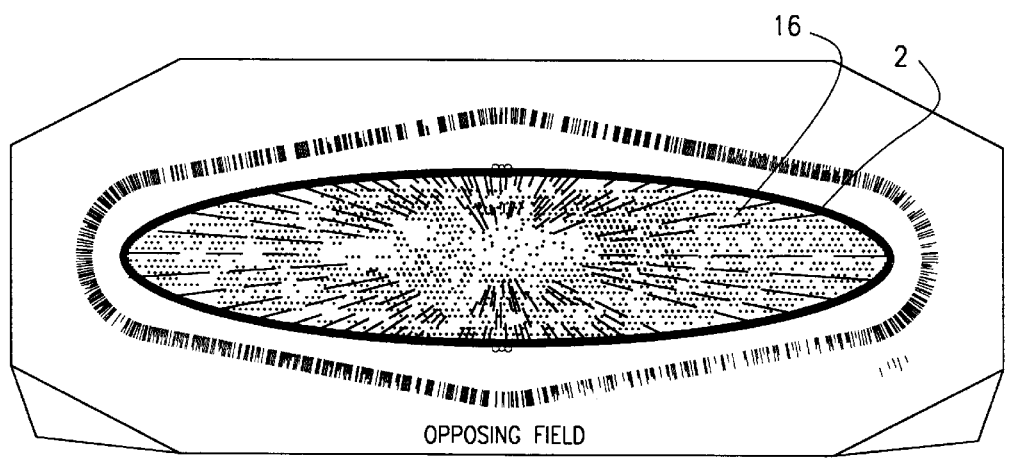
FIG. 12 is a graphic representation of an iron filing sculpture produced by a cumulative complex field generated by the preferred embodiment of the present invention.

Once the current level flowing through the coil of wire 4 is reversed, the electromagnetic field generated thereby reverses direction. In this case, the reversed direction of the electromagnetic field is in the opposite direction to the direction of the magnetic field generated by permanent magnets 1. At this time, the resulting complex field can no longer be viewed as a summation of the electromagnetic field and the magnetic field. Rather, the resulting complex field can be viewed as a difference between the electromagnetic field (generated by the current passing through the coil of wire 4) and the magnetic field (generated by the ring 2 of permanent magnets 1). FIG. 12 illustrates the resulting complex field when the direction of the electromagnetic field is opposed to the direction of the magnetic field. As can be seen, the resulting complex field has a reduced amount of flux and intensity throughout the central area of the inner portion of ring 2. In the present exemplary operation, the resulting complex field reverses direction relative to the direction of the resulting complex field as initially created.

The change in direction of the resulting complex field has a significant effect on the cells under treatment. In particular, with the resulting complex field reversing direction, the positive ions appearing along the surface of the cells are caused to collide with other ions in the cell. This ionic collision destroys or implodes the cells. The above-described steps are repeated until all of the cells to be treated have been suitably destroyed.

It has been observed that repetitive treatments of the above-identified steps substantially destroy substantially all of the cells associated with the resonant frequency in an individuals body.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A frequency generator for treating cells of a similar type, comprising:

a plurality of permanent magnets arranged in a side-by-side relationship with the magnetic north pole and the magnetic south pole of each permanent magnet being adjacent the magnetic north pole and magnetic south pole of an adjacent permanent magnet, respectively, the plurality of permanent magnets forming a ring of permanent magnets;

a wire of electrically conductive material wound substantially around the ring of permanent magnets so as to form a coil;

tubing wrapped around the ring of permanent magnets between windings of the wire;

a cooling device for introducing a flow of coolant through the tubing; and a control circuit, connected to the wire, for selectively generating a coil current for passing through the wire, the current having an AC component and a DC component, the AC component having a frequency that is programmable to substantially match a resonant frequency of the cells to be treated, the coil current creating an electromagnetic field which interacts with a magnetic field generated by the ring of permanent magnets so as to generate a complex field that is applied to the cells to be treated.

2. The frequency generator of claim 1, wherein:

the control circuit includes a frequency changer circuit for generating the AC component of the coil current, the frequency changer circuit being controlled to generate the AC component having a frequency which substantially matches the resonant frequency of the cells to be treated.

3. The frequency generator of claim 1, wherein:

the control circuit includes a rectifier circuit for receiving an AC supply signal and generating a DC component of the coil current.

4. The frequency generator of claim 3, wherein:

the rectifier circuit is selectively controlled to generate the DC component having a desired current level.

5. The frequency generator of claim 4, wherein the control circuit includes a switching circuit for selectively reversing the polarity of the DC component of the coil current.

6. The frequency generator of claim 1, further comprising:

a frame for housing the ring of permanent magnets, the wire and the tubing.

7. The frequency generator of claim 6, further comprising:

a lid member removably attached to and cooperating with the frame for enclosing the ring of permanent magnets, the wire and the tubing.

8. The frequency generator of claim 7, wherein:

the lid member and the frame define an amount of air space therewithin.

9. The frequency generator of claim 8, wherein:

the frame includes one or more air ducts disposed along the frame in fluid communication with the air space within the frame and the lid.

10. The frequency generator of claim 1, wherein:

the ring of permanent magnets includes at least one gap between two adjacent permanent magnets.

11. The frequency generator of claim 1, wherein:

the cooling device comprises a condenser unit and a pump unit in fluid communication with the tubing.

12. The frequency generator of claim 1, wherein:

the tubing is copper tubing.

13. The frequency generator of claim 1, further comprising:

a second wire wrapped around the ring of permanent magnets and connected to the control circuit for passing the coil current through the second wire.

14. The frequency generator of claim 1, wherein:

the ring of permanent magnets is substantially shaped as an ellipse.

15. The frequency generator of claim 1, wherein:

the coil current generated by the control circuit is switched between first polarity levels which generate an electromagnetic field in the same direction as the direction of the magnetic field generated by the ring of permanent magnets, and second polarity levels which generate an electromagnetic field in the opposite direction from the direction of the magnetic field.

16. A frequency generator for treating cells, comprising:

a plurality of permanent magnets arranged in a side-by-side relationship with the magnetic north pole and the magnetic south pole of each permanent magnet being adjacent the magnetic north pole and magnetic south pole of an adjacent permanent magnet, respectively, the plurality of permanent magnets forming a ring of permanent magnets;

a control circuit for selectively generating a current having an AC component and a DC component, the AC component having a frequency that is programmable to substantially match a resonant frequency of the cells to be treated;

a first wire of electrically conductive material disposed proximally to the ring of permanent magnets and having a first end and a second end connected to the control circuit for passing the current through the first wire, the first wire being disposed relative to the ring of permanent magnets such that the first wire and the current create an electromagnetic field which interacts with a magnetic field generated by the ring of permanent magnets to create a complex field within an inner portion of the ring of permanent magnets that to which the cells are subjected when placed within the inner portion;

tubing disposed proximally to the ring of permanent magnets and the first wire; and a device for introducing a cooled fluid through the tubing so as to cool the frequency generator.

17. The frequency generator of claim 16, wherein:

the first wire of electrically conductive material is wrapped around the ring of permanent magnets in a direction that is substantially orthogonal to the longitudinal axes of the permanent magnets, forming a coil.

18. The frequency generator of claim 17, wherein:

the tubing is wrapped around the ring of permanent magnets substantially intertwined with the first wire of electrically conductive material.

19. The frequency generator of claim 18, wherein:

a portion of the tubing directly contacts at least some of the permanent magnets.

20. The frequency generator of claim 16, wherein:
the device for introducing a cooled fluid comprises a condenser unit and a pump in fluid communication with the tubing.

21. The frequency generator of claim 16, wherein:
the control circuit selectively reverses the polarity of the DC component of the current.

22. The frequency generator of claim 16, further including:
a second wire of electrically conductive material disposed proximally to the ring of permanent magnets and having a first end and a second end connected to the control circuit for passing the current through the second wire, the second wire being disposed relative to the ring of permanent magnets such that the second wire and the current create an electromagnetic field which interacts with the magnetic field generated by the ring of permanent magnets and the electromagnetic field generated by the first wire to generate a complex field within an inner portion of the ring of permanent magnets to which the cells are subjected when placed within the inner portion.

23. The frequency generator of claim 22, wherein:
the first and second wires are wrapped around the ring of permanent magnets in a direction that is substantially orthogonal to the longitudinal axes of the permanent magnets, forming a pair of coils.

24. The frequency generator of claim 16, wherein:
the control circuit comprises a frequency changer circuit for generating the AC component of the current and a rectifier circuit for receiving an AC supply signal and generating the DC component of the current.

25. The frequency generator of claim 24, wherein:
the control circuit further includes a switching circuit for selectively reversing the polarity of the DC component of the current.

* * * * *